(12) United States Patent
Henn et al.

(10) Patent No.: US 10,391,195 B2
(45) Date of Patent: Aug. 27, 2019

(54) SUPER-ABSORBING POLYMERS WITH RAPID ABSORPTION PROPERTIES AND METHOD FOR PRODUCING THE SAME

(71) Applicant: EVONIK DEGUSSA GMBH, Essen (DE)

(72) Inventors: Markus Henn, Gelsenkirchen (DE); Laurent Wattebled, Dusseldorf (DE); Peter Herbe, Kevelaer (DE); Jorg Harren, Marl (DE); Christoph Loick, Duisburg (DE)

(73) Assignee: Evonik Degussa GmbH, Essen (DE)

( * ) Notice: Subject to any disclaimer, the term of this patent is extended or adjusted under 35 U.S.C. 154(b) by 1018 days.

(21) Appl. No.: 14/352,171

(22) PCT Filed: Nov. 12, 2012

(86) PCT No.: PCT/EP2012/072360
§ 371 (c)(1),
(2) Date: Apr. 16, 2014

(87) PCT Pub. No.: WO2013/072269
PCT Pub. Date: May 23, 2013

(65) Prior Publication Data
US 2014/0257223 A1   Sep. 11, 2014

(30) Foreign Application Priority Data

Nov. 17, 2011 (DE) .......................... 10 2011 086 522

(51) Int. Cl.
| | | |
|---|---|---|
| *A61L 15/24* | (2006.01) | |
| *A61L 15/42* | (2006.01) | |
| *A61L 15/60* | (2006.01) | |
| *C08J 3/12* | (2006.01) | |
| *C08L 33/08* | (2006.01) | |

(52) U.S. Cl.
CPC .............. *A61L 15/24* (2013.01); *A61L 15/42* (2013.01); *A61L 15/425* (2013.01); *A61L 15/60* (2013.01); *C08J 3/12* (2013.01); *C08J 2300/14* (2013.01); *Y10T 156/10* (2015.01)

(58) Field of Classification Search
CPC ............................. A61L 15/42; C08J 2300/12
See application file for complete search history.

(56) References Cited

U.S. PATENT DOCUMENTS

| | | |
|---|---|---|
| 4,076,663 A | 2/1978 | Masuda et al. |
| 4,131,576 A | 12/1978 | Iovine et al. |
| 4,179,367 A | 12/1979 | Barthell et al. |
| 4,286,082 A | 8/1981 | Tsubakimoto et al. |
| 4,340,706 A | 7/1982 | Obayashi et al. |
| 4,587,308 A | 5/1986 | Makita et al. |
| 5,409,771 A | 4/1995 | Dahmen et al. |
| 5,433,715 A | 7/1995 | Tanzer et al. |
| 5,562,646 A | 10/1996 | Goldman et al. |
| 5,599,335 A | 2/1997 | Goldman et al. |
| 5,610,220 A | 3/1997 | Klimmek et al. |
| 5,669,894 A | 9/1997 | Goldman et al. |
| 5,672,633 A | 9/1997 | Brehm et al. |
| 5,712,316 A | 1/1998 | Dahmen et al. |
| 5,985,944 A | 11/1999 | Ishizaki et al. |
| 6,060,557 A | 5/2000 | Dahmen et al. |

(Continued)

FOREIGN PATENT DOCUMENTS

| | | |
|---|---|---|
| CN | 1140458 | 1/1997 |
| DE | 2706135 A1 | 8/1978 |

(Continued)

OTHER PUBLICATIONS

German language International Search Report dated Mar. 29, 2013 in PCT/EP2012/072360 (5 pages).
International Search Report dated May 29, 2013 in PCT/EP2012/072360 (4 pages).
Naumann et al., U.S. Appl. No. 14/354,372, filed Apr. 25, 2014.
Wattebled et al., U.S. Appl. No. 14/352,091, filed Apr. 16, 2014.
Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).
Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).
Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).

(Continued)

*Primary Examiner* — Melissa A Rioja
(74) *Attorney, Agent, or Firm* — Bernard Lau; Jason S. Ngui; Linda S. Li

(57) ABSTRACT

The present invention relates to a particulate absorbent polymer material having:
i) a maximum $APC_{i \times 10\ sec}$ value $\geq 1.6$) for at least one number i selected from the group of integers from 2 to 12 ($=APC_{max}$); or
ii) a value $\geq 12$ for the sum total of all $APC_{i \times 10\ sec}$ values for all numbers i from the group of integers from 2 to 12 ($=APC_{sum}$);
wherein the $APC_{i \times 10\ sec}$ value is:

$$APC_{i \times 10\ sec} = QI_{i \times 10\ sec}\ \text{value}^2 \times PI_{i \times 10\ sec}\ \text{value}$$

where
the $QI_{i \times 10\ sec}$ value is the swell index and i×10 seconds after adding the 0.9% by weight NaCl solution, and
the $PI_{i \times 10\ sec}$ value is the permeability index and i×10 seconds after adding the 0.9% by weight NaCl solution.

12 Claims, 5 Drawing Sheets

(56) References Cited

U.S. PATENT DOCUMENTS

| | | |
|---|---|---|
| 6,251,960 B1 | 6/2001 | Ishizaki et al. |
| 6,403,700 B1 | 6/2002 | Dahmen et al. |
| 6,605,673 B1 | 8/2003 | Mertens et al. |
| 6,620,889 B1 | 9/2003 | Mertens et al. |
| 6,623,848 B2 | 9/2003 | Brehm et al. |
| 6,831,142 B2 | 12/2004 | Mertens et al. |
| 6,849,665 B2 | 2/2005 | Frenz et al. |
| 6,972,011 B2 | 12/2005 | Maeda et al. |
| 7,157,141 B2 | 1/2007 | Inger et al. |
| 7,163,966 B2 | 1/2007 | Joy et al. |
| 7,179,862 B2 | 2/2007 | Mertens et al. |
| 7,285,599 B2 | 10/2007 | Mertens et al. |
| 7,507,475 B2 | 3/2009 | Inger et al. |
| 7,541,395 B2 | 6/2009 | Reimann et al. |
| 7,572,864 B2 | 8/2009 | Mertens et al. |
| 7,625,957 B2 | 12/2009 | Harren et al. |
| 7,728,079 B2 | 6/2010 | Harren et al. |
| 7,833,624 B2 | 11/2010 | Harren et al. |
| 7,893,134 B2 | 2/2011 | Reimann et al. |
| 8,048,942 B2 | 11/2011 | Fricker et al. |
| 8,063,121 B2 | 11/2011 | Fricker et al. |
| 8,071,202 B2 | 12/2011 | Furno et al. |
| 8,198,385 B2 | 6/2012 | Gartner et al. |
| 8,202,957 B2 | 6/2012 | Stueven et al. |
| 8,252,873 B1 | 8/2012 | Gartner et al. |
| 8,349,913 B2 | 1/2013 | Harren et al. |
| 8,357,766 B2 | 1/2013 | Fricker et al. |
| 8,389,658 B2 | 3/2013 | Stueven et al. |
| 8,420,567 B1 | 4/2013 | Naumann et al. |
| 8,445,596 B2 | 5/2013 | Mertens et al. |
| 8,476,189 B1 | 7/2013 | Naumann et al. |
| 8,653,210 B2 | 2/2014 | Fricker et al. |
| 8,658,146 B2 | 2/2014 | Furno et al. |
| 8,686,216 B2 | 4/2014 | Wattebled et al. |
| 8,765,906 B2 | 7/2014 | Watanabe et al. |
| 8,791,210 B2 | 7/2014 | Sakamoto et al. |
| 8,921,641 B2 | 12/2014 | Ehrnsperger et al. |
| 8,962,911 B2 | 2/2015 | Ehrnsperger et al. |
| 9,060,904 B2 | 6/2015 | Hundorf et al. |
| 9,074,030 B2 | 7/2015 | Takaai et al. |
| 2002/0128618 A1 | 9/2002 | Frenz et al. |
| 2003/0139716 A1 | 7/2003 | Falk |
| 2005/0090586 A1 | 4/2005 | Kang et al. |
| 2005/0288641 A1 | 12/2005 | Soerens |
| 2007/0238806 A1 | 10/2007 | Mitsukami et al. |
| 2008/0312618 A1* | 12/2008 | Hundorf ............ A61F 13/5323 604/366 |
| 2009/0227741 A1 | 9/2009 | Walden et al. |
| 2010/0036004 A1 | 2/2010 | Harren et al. |
| 2010/0099781 A1 | 4/2010 | Tian et al. |
| 2011/0009272 A1 | 1/2011 | Wattebled et al. |
| 2012/0001122 A1 | 1/2012 | Wattebled et al. |
| 2012/0145956 A1 | 6/2012 | Walden et al. |
| 2012/0219633 A1 | 8/2012 | Sowemimo-Coker |
| 2012/0258851 A1 | 10/2012 | Nakatsuru et al. |
| 2012/0302445 A1 | 11/2012 | Rudolph et al. |
| 2012/0309905 A1 | 12/2012 | Fricker et al. |
| 2012/0318046 A1 | 12/2012 | Ehrnsperger et al. |
| 2013/0011601 A1 | 1/2013 | Fenske |
| 2013/0012899 A1 | 1/2013 | Fenske |
| 2013/0026412 A1 | 1/2013 | Machida et al. |
| 2014/0045683 A1 | 2/2014 | Loick et al. |
| 2014/0054497 A1 | 2/2014 | Wattebled et al. |
| 2014/0121322 A1 | 5/2014 | Fricker et al. |
| 2014/0296465 A1 | 10/2014 | Sakamoto et al. |
| 2014/0324008 A1 | 10/2014 | Hundorf et al. |
| 2015/0080822 A1 | 3/2015 | Ehrnsperger et al. |
| 2015/0096938 A1 | 4/2015 | Sowemimo-Coker |
| 2015/0126948 A1 | 5/2015 | Ehrnsperger et al. |

FOREIGN PATENT DOCUMENTS

| | | |
|---|---|---|
| DE | 2840010 A1 | 6/1979 |
| DE | 3503458 A1 | 8/1985 |
| DE | 3713601 A1 | 11/1988 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19529348 A1 | 2/1997 |
| DE | 102009049450 A1 | 6/2011 |
| EP | 0826349 A2 | 3/1998 |
| EP | 2018877 A1 | 1/2009 |
| EP | 1225857 B1 | 2/2009 |
| EP | 2383115 A1 | 11/2011 |
| EP | 2565219 A1 | 3/2013 |
| EP | 2157956 B1 | 7/2013 |
| JP | H09-504207 A | 4/1997 |
| JP | 2003-529647 A | 10/2003 |
| JP | 3768235 B2 | 4/2006 |
| JP | 2010529900 A | 9/2010 |
| JP | 2014-514936 A | 6/2014 |
| JP | 2014-515987 A | 7/2014 |
| WO | 9511651 A1 | 5/1995 |
| WO | 9511652 A1 | 5/1995 |
| WO | 9511653 A1 | 5/1995 |
| WO | 9511654 A1 | 5/1995 |
| WO | 9605234 A1 | 2/1996 |
| WO | 9617884 A1 | 6/1996 |
| WO | 9711659 A1 | 4/1997 |
| WO | 9837846 A1 | 9/1998 |
| WO | 9934843 A1 | 7/1999 |
| WO | 0115646 A1 | 3/2001 |
| WO | 0115647 A1 | 3/2001 |
| WO | 0189439 A1 | 11/2001 |
| WO | 02053198 A1 | 7/2002 |
| WO | 2004037903 A2 | 5/2004 |
| WO | 2004071363 A1 | 8/2004 |
| WO | 2006109844 A1 | 10/2006 |
| WO | 2008009580 A1 | 1/2008 |
| WO | 2008117109 A1 | 10/2008 |
| WO | 2008155699 A1 | 12/2008 |
| WO | 2008155701 A2 | 12/2008 |
| WO | 2008155702 A1 | 12/2008 |
| WO | 2008155710 A1 | 12/2008 |
| WO | 2008155711 A1 | 12/2008 |
| WO | 2008155722 A2 | 12/2008 |
| WO | 2009011717 A1 | 1/2009 |
| WO | 2010095427 A1 | 8/2010 |
| WO | 2010115671 A1 | 10/2010 |
| WO | WO 2010115671 A1 * | 10/2010 ............ A61F 13/00 |
| WO | 2011078298 A1 | 6/2011 |
| WO | 2011120504 A2 | 10/2011 |
| WO | 2011136301 A1 | 11/2011 |

OTHER PUBLICATIONS

Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).

Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

* cited by examiner

US 10,391,195 B2

SUPER-ABSORBING POLYMERS WITH RAPID ABSORPTION PROPERTIES AND METHOD FOR PRODUCING THE SAME

This application is a national stage application under 35 U.S.C. § 371 of International Application No. PCT/EP2012/072360 filed 12 Nov. 2012, which claims priority to German Application No. DE 10 2011 086 522.5 filed 17 Nov. 2011, the disclosures of which are expressly incorporated herein by reference.

FIELD

The invention relates to a particulate absorbent polymer material, a process for producing a particulate absorbent polymer material, an absorbent core containing a particulate absorbent polymer material, a hygiene article, a process for producing an absorbent core and also an absorbent core obtainable by this process.

BACKGROUND

Superabsorbents are water-insoluble, crosslinked polymers capable of imbibing and retaining, under pressure, large amounts of aqueous fluids, especially bodily fluids, preferably urine or blood, by swelling and forming hydrogels. In general, these imbibitions of fluid amount to not less than 10 times or even not less than 100 times the dry weight of the superabsorbents, or superabsorbent compositions, for water. Owing to these characteristic properties, these polymers have their main application in the absorbent cores of hygiene articles such as baby diapers, incontinence products or sanitary napkins. A comprehensive overview of superabsorbents and superabsorbent compositions, their use and their production is provided by F. L. Buchholz and A. T. Graham (editors) in "*Modern Superabsorbent Polymer Technology*", Wiley-VCH, New York, 1998.

Superabsorbents are generally prepared by free-radical polymerization of acid-functional, usually partially neutralized monomers in the presence of crosslinkers. By varying the monomer composition, the crosslinkers and also the polymerization conditions and the processing conditions for the hydrogel obtained after polymerization, polymers having different absorption properties can be prepared. Further possibilities are offered by the production of graft polymers for example by using chemically modified starch, cellulose and polyvinyl alcohol as described in DE-A-26 12 846.

The current trend in diaper construction in particular is to produce ever thinner absorbent cores having a reduced cellulose fiber content and an increased superabsorbent content. The advantage of thinner designs manifests itself not only in an improved wearing comfort, but also in reduced costs for packaging and stockholding. The latest generation of absorbent cores, which is described for example in WO-A-2008/155722, WO-A-2008/155711, WO-A-2008/155710, WO-A-2008/155702, WO-A-2008/155701, WO-A-2008/155699, EP-A-1 225 857, WO-A-01/15647, WO-A-2011/120504, DE-A-10 2009 049 450, WO-A-2008/117109, WO-A-97/11659, EP-A-0 826 349, WO-A-98/37846, WO-A-95/11653, WO-A-95/11651, WO-A-95/11652, WO-A-95/11654, WO-A-2004/071363 or WO-A-01/89439, is essentially cellulose-free (and hence the diapers of this type are also referred to as fluffless diapers). Superabsorbent particle immobilization, effected in cellulose-containing absorbent cores by the cellulose fibers, can be achieved in this latest generation of absorbent cores by, for example, thermoplastic fibers immobilizing the superabsorbent particles on a substrate surface.

The trend towards ever thinner diaper designs and the disappearance of the temporary fluid-storing and conducting function of cellulose fibers has resulted in a distinct change in the performance profile required of superabsorbents. What is of decisive importance now is the ability of the hydrogel to prevent leakage of urine directly in the course of micturation. This is achieved by the property of the superabsorbent/hydrogel whereby the fluid is sufficiently imbibed, and dispersed in the gel layer, during swelling while at the same time the amount of unbound urine in the diaper is minimized. Advantageous superabsorbents also have good transfer properties and so ensure optimum utilization of the entire hygiene article.

However, prior art superabsorbents are insufficiently suitable for use in the above-described new generation of cellulose-free diaper designs.

The problem addressed by the present invention was therefore that of overcoming the superabsorbent-related disadvantages that surrender to the prior art.

More particularly, the problem addressed by the present invention was that of providing superabsorbents that are particularly advantageous for use in absorbent cores having a low cellulose fiber content, for example in the cellulose-free designs described in WO-A-2008/155722, WO-A-2008/155711, WO-A-2008/155710, WO-A-2008/155702, WO-A-2008/155701 or WO-A-2008/155699.

Another problem addressed by the present invention was that of providing a selection process for selecting, from the multiplicity of currently known superabsorbent materials, those superabsorbents capable of being reliably used in the cellulose-free designs described in WO-A-2008/155722, WO-A-2008/155711, WO-A-2008/155710, WO-A-2008/155702, WO-A-2008/155701 or WO-A-2008/155699 for example.

SUMMARY

A contribution to solving the problems defined at the beginning is made by a particulate absorbent polymer material having at least one of the following properties:
i) a maximum $APC_{i \times 10\ sec}$ value $\geq 1.6$, preferably 2.0 and more preferably $\geq 2.4$ for at least one number i selected from the group of integers from 2 to 12 (=$APC_{max}$ value), wherein an $APC_{max}$ value of preferably 14.0, more preferably 12.0 and most preferably 10.0 is not exceeded;
ii) a value $\geq 12$, preferably 18 and more preferably $\geq 24$ for the sum total of all $APC_{i \times 10\ sec}$ values for all numbers i from the group of integers from 2 to 12 (=$APC_{sum}$); wherein an $APC_{sum}$ value of preferably 55, more preferably 50 and most preferably 45 is not exceeded;
wherein the $APC_{i \times 10\ sec}$ value is defined as follows:

$$APC_{i \times 10\ sec} = QI_{i \times 10\ sec}\ \text{value}^2 \times PI_{i \times 10\ sec}\ \text{value}$$

where
the $QI_{i \times 10\ sec}$ value is the value of the swell index determined as per the herein described test method i×10 seconds after adding the 0.9% by weight NaCl solution, and
the $PI_{i \times 10\ sec}$ value is the value of the permeability index determined as per the herein described test method i×10 seconds after adding the 0.9% by weight NaCl solution.

In a particular embodiment of the particulate absorbent polymer materials of the present invention, these have a WSP 241.3 (test method of the Worldwide Strategic Partners EDANA and INDA) centrifuge retention capacity (CRC) of not less than 22 g/g, preferably not less than 24 g/g, more preferably not less than 26 g/g and most preferably not less than 28 g/g.

In a further particular embodiment of the particulate absorbent polymer materials of the present invention, these have a WSP 242.3 absorption under pressure (AUP) of 0.7 psi of not less than 16 g/g, preferably not less than 18 g/g, more preferably not less than 20 g/g and most preferably not less than 22 g/g.

Particulate absorbent polymer materials preferred according to the present invention are fibers, foams or particles, of which fibers and particles are preferable and particles are more preferable.

DETAILED DESCRIPTION

Polymer fibers preferred according to the present invention are dimensioned such that they can be incorporated in or as yarns for textiles and also directly in textiles. It is preferable according to the present invention for the polymer fibers to have a length in the range from 1 to 500 mm, preferably from 2 to 500 mm and more preferably from 5 to 100 mm and a diameter in the range from 1 to 200 denier, preferably from 3 to 100 denier and more preferably from 5 to 60 denier.

Particulate absorbent polymer materials preferred according to the present invention are dimensioned such that they have a WSP 220.2 mean particle size in the range from 10 to 3000 µm, preferably from 20 to 2000 µm and more preferably from 150 to 850 µm. It is especially preferable here for the proportion of polymer particles having a particle size in the range from 300 to 600 µm to amount to not less than 50% by weight, more preferably not less than 65% by weight and most preferably not less than 80% by weight, based on the total weight of water-absorbing polymer particles.

It is further preferable according to the present invention for the particulate absorbent polymer materials of the present invention to be based on partially neutralized crosslinked acrylic acid. It is particularly preferable in this context for the particulate absorbent polymer materials of the present invention to be crosslinked polyacrylates with a microporous structure which consist of monomers bearing carboxylate groups to an extent of not less than 50% by weight, preferably not less than 70% by weight and more preferably not less than 90% by weight, all based on the weight of the polymer materials. It is further preferable according to the present invention for the particulate absorbent polymer materials of the present invention to be based to an extent not less than 50% by weight, preferably not less than 70% by weight, both based on the weight of the polymer materials, on polymerized acrylic acid which is preferably not less than 20 mol %, more preferably not less than 50 mol % and even more preferably from 60 to 85 mol % neutralized.

The particulate absorbent polymer materials of the present invention are preferably obtainable by a process containing the steps of:
i) free-radically polymerizing an aqueous monomer solution containing a polymerizable, monoethylenically unsaturated acid-functional monomer ($\alpha 1$) or salt thereof, optionally a monoethylenically unsaturated monomer ($\alpha 2$) polymerizable with the monomer ($\alpha 1$), a blowing or expanding agent ($\alpha 3$) and also at least one crosslinker ($\alpha 4$) to obtain a hydrogel having a microporous structure;
ii) optionally comminuting the hydrogel having a microporous structure;
iii) drying the optionally comminuted hydrogel having a microporous structure to obtain particulate absorbent polymer materials having a microporous structure;
iv) optionally grinding and screening off the resulting particulate absorbent polymer materials having a microporous structure;
v) surface-postcrosslinking the resulting particulate absorbent polymer materials having a microporous structure with a crosslinker having two or more functional groups capable of reacting with the acid groups on the surface of the polymer materials, wherein the surface of the polymer materials is brought into contact with aluminum salts before, during or after the postcrosslinking.

In process step i) initially an aqueous monomer solution containing a polymerizable, monoethylenically unsaturated acid-functional monomer ($\alpha 1$) or a salt thereof, optionally a monoethylenically unsaturated monomer ($\alpha 2$) polymerizable with the monomer ($\alpha 1$), a blowing or expanding agent ($\alpha 3$) and also at least one crosslinker ($\alpha 4$) is free-radically polymerized to obtain a polymer gel. The monoethylenically unsaturated acid-functional monomers ($\alpha 1$) may be in a partially or completely, preferably partially, neutralized state. Preferably, the monoethylenically unsaturated acid-functional monomers ($\alpha 1$) are in a neutralized state to an extent not less than 25 mol %, more preferably not less than 50 mol % and even more preferably to an extent of 50-80 mol %. The disclosure of DE 195 29 348 A1 in this context is hereby incorporated herein by reference. Neutralization may also be effected partly or wholly after the polymerization. Neutralization may further be effected using alkali metal hydroxides, alkaline earth metal hydroxides, ammonia and also carbonates and bicarbonates. Any further base capable of combining with the acid to form a water-soluble salt is also conceivable. Mixed neutralization with different bases is also conceivable. Preference is given to neutralization with a combination of carbonates and/or bicarbonates (which also act as blowing or expanding agents) and alkali metal hydroxides, more preferably with a combination of sodium carbonate and sodium hydroxide.

Moreover, in the inventive water-absorbing polymer structures, the free acid groups may predominate, such that this polymer structure has a pH in the acidic range. This acidic water-absorbing polymer structure can be at least partly neutralized by a polymer structure with free basic groups, preferably amine groups, which is basic compared to the acidic polymer structure. These polymer structures are referred to in the literature as "*Mixed-Bed Ion-Exchange Absorbent Polymers*" (MBIEA polymers) and are disclosed, inter alia, in WO 99/34843 A1. The disclosure of WO 99/34843 A1 is hereby incorporated by reference and is therefore considered to form part of the disclosure. In general, MBIEA polymers constitute a composition which firstly includes basic polymer structures which are capable of exchanging anions, and secondly an acidic polymer structure compared to the basic polymer structure, which is capable of exchanging cations. The basic polymer structure has basic groups and is typically obtained by the polymerization of monomers which bear basic groups or groups which can be converted to basic groups. These monomers are primarily those which have primary, secondary or tertiary amines or the corresponding phosphines or at least two of the above functional groups. This group of monomers includes especially ethyleneamine, allylamine, diallylamine, 4-aminobutene, alkyloxycyclines, vinylformamide, 5-aminopentene, carbodiimide, formaldacine, melamine and the like, and the secondary or tertiary amine derivatives thereof.

Preferred monoethylenically unsaturated monomers bearing acid groups (α1) are preferably those compounds specified as ethylenically unsaturated monomers bearing acid groups (α1) in WO 2004/037903 A2, which is hereby incorporated by reference and is therefore considered to be part of the disclosure. Particularly preferred monoethylenically unsaturated monomers bearing acid groups (α1) are acrylic acid and methacrylic acid, acrylic acid being the most preferred.

The monoethylenically unsaturated monomers (α2) used, which are copolymerizable with the monomers (α1), may be acrylamides, methacrylamides or vinylamides. Further preferred co-monomers are especially those which in the—bearing monomers (α1) are preferably those compounds which in WO 2004/037903 A2 are mentioned as co-monomers (α2).

Copolymerizable, monoethylenically unsaturated surfactants are used as co-monomers (α2) in a special embodiment of a process for producing the particulate absorbent polymer materials of the present invention. These special surfactants include functional groups that are polymerizable. Preferred chemical structures for these surfactants are

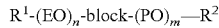

where $R^1$ and $R^2$ are methyl, ethyl, n-propyl, isopropyl, n-butyl, isobutyl, n-pentyl, 2-methylbutyl, 2,2-dimethylpropyl, —OH, acetyl or allyl and n is =2 to 20 and m is =2 to 20. EO and PO are respectively hydrophilic and hydrophobic blocks to generate surfactant properties. Reactive allyl groups are preferred for R1 or R2, since they, in accordance with the present invention, interpolymerize later as acryloyl group and are more stable in hydrolysis. The commercial Pluriol A 23 R product used by BASF AG may be mentioned as an example of such a copolymerizable surfactant.

Useful blowing or expanding agents (α3) include more particularly any assistant material known to a person skilled in the art which, in the polymerization, favors the formation of voids, as of pores for example, and hence the formation of a microporous structure in the polymer gel. Useful blowing agents include more particularly those blowing agents disclosed for instance in EP-A-0-644 207 as preferred blowing agents. Especially blowing agents based on carbonates come into consideration here. On heating, the blowing agent releases carbon dioxide which is in a dissolved or dispersed state in the carbonate-containing monomer solution. The blowing agent may be any carbonate- or bicarbonate-containing salt or mixed salt and may comprise carbon dioxide as a gas or solid material sodium carbonate, potassium carbonate, ammonium carbonate, magnesium carbonate or magnesium hydroxycarbonates, calcium carbonate, barium carbonate and bicarbonates and their hydrates or other cations, and also naturally occurring carbonates such as dolomite and its mixtures. Preferred carbonate blowing agents are $MgCO_3$, $(NH4)_2CO_3$ $Na_2CO_3$ and mixtures thereof. It is further preferable in this connection for about 0.05% by weight to about 5.0% by weight of blowing agent to be added based on the weight of the optionally partially neutralized monomer (α1) and more preferably based on the optionally partially neutralized acrylic acid. It is most preferable for about 0.2% by weight to about 3.0% by weight of blowing agent to be added. Blowing agents may also be encapsulated, as described in U.S. Pat. No. 7,163,966 for example.

In addition to or in lieu of the blowing agents described above, hollow bodies having a shell of organic or inorganic material can also be added to the monomer solution for the purposes of forming voids in polymer material, as described in WO-A-2010/115671. Hollow bodies having a shell of an organic material are preferably hollow bodies selected from the following group:

hollow bodies having a shell of a polymeric thermoplastic material;

hollow bodies having a shell of a polymeric, non-thermoplastic material.

Generally, useful hollow bodies include gas-filled microballoons based on thermoplastic or non-thermoplastic polymers, polyelectrolyte multilayer capsules, hollow spheres based on thermoplastic or non-thermoplastic polymers, microsphere particles based on thermoplastic polymers and as available for example under the EXPANCEL® brand name, or hollow body having a shell of polycrystalline aluminum oxide.

Useful crosslinkers (α4) preferably likewise include those compounds specified in WO 2004/037903 A2 as crosslinkers (α3) Does this enumeration relate to WO2004037903? If not, (α4) would be correct. Among these crosslinkers, particular preference is given to water-soluble crosslinkers. The most preferred are N,N'-methylenebisacrylamide, polyethylene glycol di(meth)acrylates, triallylmethylammonium chloride, tetraallylammonium chloride, and allyl nonaethylene glycol acrylate prepared with 9 mol of ethylene oxide per mole of acrylic acid.

In addition to the monomers (α1) and optionally (α2), the blowing or expanding agents (α3) and also the at least one crosslinker (α4), the monomer solution may also contain water-soluble polymers (α5). Preferred water-soluble polymers comprise partly or fully hydrolyzed polyvinyl alcohol, polyvinylpyrrolidone, starch or starch derivatives, polyglycols or polyacrylic acid. The molecular weight of these polymers is uncritical provided that they are water-soluble. Preferred water-soluble polymers are starch or starch derivatives or polyvinyl alcohol. The water-soluble polymers, preferably synthetic water-soluble polymers such as polyvinyl alcohol, can not only serve as the graft base for the monomers to be polymerized. It is also conceivable to mix these water-soluble polymers with the polymer gel only after the polymerization, or with the already dried, water-absorbing polymer gel.

In addition, the monomer solution may also comprise auxiliaries (α6), which auxiliaries include especially the initiators or complexing agents which may be required for the polymerization, for example EDTA.

Useful solvents for the monomer solution include water, organic solvents or mixtures of water and organic solvents, the selection of the solvent depending especially also on the manner of the polymerization.

The relative amount of monomers (α1) and (α2), of blowing or expanding agents (α3) and also of crosslinkers (α4) and water-soluble polymers (α5) and auxiliaries (α6) in the monomer solution is preferably selected such that the particulate absorbent polymer material having a microporous structure obtained after drying in process step iii) is based to an extent of 20 to 99.999% by weight, preferably to an extent of 55 to 98.99% by weight and more preferably to an extent of 70 to 98.79% by weight on the monomers (α1), to an extent of 0 to 80% by weight, preferably to an extent of 0 to 44.99% by weight and more preferably to an extent of 0.1 to 44.89% by weight on the monomers (α2), to an extent of 0 to 5% by weight, preferably to an extent of 0.001 to 3% by weight and more preferably to an extent of 0.01 to 2.5% by weight on the crosslinkers (α4), to an extent of 0 to 30% by weight, preferably to an extent of 0 to 5% by weight and more preferably to an extent of 0.1 to 5% by weight on the water-soluble polymers (α5), to an extent of 0 to 20% by weight, preferably to an extent of 0 to 10% by weight and more preferably to an extent of 0.1 to 8% by weight on the auxiliaries (α6), and to an extent of 0.5 to 25% by weight, preferably to an extent of 1 to 10% by weight and more preferably to an extent of 3 to 7% by weight on water (α7), where the sum of the weights (α1) to (α7) is 100% by weight. Optimum values in respect of the concentration especially of the monomers, the blowing or expanding agents, crosslinkers and water-soluble polymers, in the monomer solution can be determined by simple preliminary tests or else inferred from the prior art, especially publications U.S. Pat. No. 4,286,082, DE-A-27 06 135, U.S. Pat. No. 4,076,663, DE-A-35 03 458, DE 40 20 780 C1, DE-A-42 44 548, DE-A-43 33 056 and DE-A-44 18 818. For the free-radical polymerization of the monomer solution, useful polymerization processes may in principle be all of those known to those skilled in the art. For example, mention should be made in this context of solution polymerization, which is preferably effected in kneading reactors such as extruders or continuously on a polymerization belt spray polymerization, inverse emulsion polymerization and inverse suspension polymerization.

The solution polymerization is preferably performed in water as the solvent. The solution polymerization can be effected continuously or batch wise. The prior art discloses a broad spectrum of possible variations with regard to reaction conditions, such as temperatures, type and amount of the initiators, and the reaction solution. Typical processes are described in the following patents: U.S. Pat. No. 4,286,082, DE-A-27 06 135 A1, U.S. Pat. No. 4,076,663, DE-A-35 03 458, DE 40 20 780 C1, DE-A-42 44 548, DE-A-43 33 056, DE-A-44 18 818. The disclosures are hereby incorporated by reference and are therefore considered to form part of the disclosure.

The polymerization is triggered by an initiator, as is generally customary. The initiators used to initiate the polymerization may be all initiators which form free radicals under the polymerization conditions and are typically used in the production of superabsorbents. Initiation of the polymerization by the action of electron beams on the polymerizable aqueous mixture is also possible. The polymerization can, however, also be triggered in the absence of initiators of the type mentioned above by the action of high-energy radiation in the presence of photoinitiators. Polymerization initiators may be present dissolved or dispersed in the monomer solution. Useful initiators include all compounds which decompose to free radicals and are known to the person skilled in the art. These include especially those initiators which are already mentioned in WO-A-2004/037903 as possible initiators. Particular preference is given to producing the water-absorbing polymer structures using a redox system consisting of hydrogen peroxide, sodium peroxodisulphate and ascorbic acid.

Inverse suspension and emulsion polymerization can also be employed to produce the inventive particulate absorbent polymer materials. In these processes, an aqueous, partly neutralized solution of the monomers (α1) and the blowing or expanding agents (α3) and also optionally containing the further monomers (α2), the water-soluble polymers (α5) and auxiliaries (α6), is dispersed with the aid of protective colloids and/or emulsifiers in a hydrophobic organic solvent, and the polymerization is initiated by means of free-radical initiators. The crosslinkers (α4) are either dissolved in the monomer solution and are metered in together with it, or else are added separately and optionally during the polymerization. Optionally, a water-soluble polymer (α5) is added as a graft base via the monomer solution, or by direct initial charging into the oil phase. Subsequently, the water is removed from the mixture as an azeotrope and the polymer is filtered off.

In addition, both in the case of solution polymerization and in the case of inverse suspension and emulsion polymerization, the crosslinking can be effected by copolymerization of the polyfunctional crosslinker (α4) dissolved in the monomer solution and/or by reaction of suitable crosslinkers with functional groups of the polymer during the polymerization steps. The processes are described, for example, in publications U.S. Pat. No. 4,340,706, DE-A-37 13 601, DE-A-28 40 010 and WO-A-96/05234, the corresponding disclosure of which is hereby incorporated by reference.

In process step ii), the hydrogel having a microporous structure obtained in process step i) is optionally comminuted, this comminution being effected especially when the polymerization is performed by means of a solution polymerization. The comminution can be effected by means of comminution apparatus known to those skilled in the art, for instance a meat grinder.

In process step iii), the hydrogel having a microporous structure which has optionally been comminuted beforehand is dried. The hydrogel is preferably dried in suitable driers or ovens. Examples include rotary tube ovens, fluidized bed driers, pan driers, paddle driers or infrared driers. It is additionally preferred in accordance with the invention that the hydrogel is dried in process step iii) down to a water content of 0.5 to 25% by weight, preferably of 1 to 10% by weight, the drying temperatures typically being within a range from 100 to 200° C.

In process step iv), the particulate absorbent polymer materials with a microporous structure which are obtained in process step iii), especially when they have been obtained by solution polymerization, can be ground and screened off to the desired particle size specified at the outset. The dried absorbent polymer materials with a microporous structure are preferably ground in suitable mechanical comminuting devices, for example a ball mill, while screening off can be effected for example by using screens of suitable mesh size.

In process step v), the optionally ground and screened-off particulate absorbent polymer materials having a microporous structure are surface postcrosslinked with a crosslinker having two or more functional groups capable of reacting with the acid groups on the surface of the polymer materials, and the surface of the polymer materials is brought into contact with aluminum salts, preferably with aluminum lactate and/or aluminum sulphate, before, during or after the postcrosslinking.

For surface postcrosslinking, the dried and optionally ground and screened-off particulate absorbent polymer materials having a microporous structure, from process steps iii) or iv), or else the undried, but preferably already comminuted hydrogel having a microporous structure, from process step ii), are brought into contact with a preferably organic, chemical surface postcrosslinker. Especially when the postcrosslinker is not liquid under the postcrosslinking conditions, it is preferably contacted with the particulate absorbent polymer material or the polymer gel in the form of a fluid comprising the postcrosslinker and a solvent. The solvents used are preferably water, water-miscible organic solvents, for instance methanol, ethanol, 1-propanol, 2-propanol or 1-butanol or mixtures of at least two of these solvents, water being the most preferred solvent. It is additionally preferred that the postcrosslinker is present in the fluid in an amount within a range from 5 to 75% by weight, more preferably 10 to 50% by weight and most preferably 15 to 40% by weight, based on the total weight of the fluid.

The contacting of the particulate absorbent polymer material having a microporous structure or of the optionally comminuted hydrogel having a microporous structure, with the fluid containing the postcrosslinker is preferably effected by thorough mixing of the fluid with the polymer material and hydrogel, respectively.

Suitable mixing units for applying the fluid are, for example, the Patterson Kelley mixer, DRAIS turbulent mixers, Lödige mixers, Ruberg mixers, screw mixers, pan mixers and fluidized bed mixers, and also continuous vertical mixers in which the polymer material is mixed at high frequency by means of rotating blades (Schugi mixer).

The particulate absorbent polymer material having a microporous structure, or the hydrogel, is preferably contacted at postcrosslinking with not more than 20% by weight, more preferably with not more than 15% by weight, even more preferably with not more than 10% by weight and yet even more preferably with not more than 5% by weight of solvent, preferably water.

In the case of polymer materials in the form of preferably spherical particles, it is further preferable according to the present invention for the contacting to be effected such that only the outer region but not the inner region of the particulate polymer materials is brought into contact with the fluid and hence the postcrosslinker.

Postcrosslinkers are preferably understood to mean compounds which have at least two functional groups which can react with the acid groups on the surface of the polymer material in a condensation reaction (=condensation crosslinkers), in an addition reaction or in a ring-opening reaction. Preferred postcrosslinkers are those specified in WO-A-2004/037903 as crosslinkers of crosslinker classes II.

Among these compounds, particularly preferred postcrosslinkers are condensation crosslinkers, for example diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

Once the particulate absorbent polymer material having a microporous structure, or the hydrogels having a microporous structure, have been brought into contact with the postcrosslinker or with the fluid including the postcrosslinker, they are heated to a temperature in the range from 50 to 300° C., preferably 75 to 275° C. and more preferably 150 to 250° C., such that, preferably as a result of which, the outer region of the particles of the polymer material is more highly crosslinked compared to the inner region (=postcrosslinking), and, when a hydrogel are used, they are simultaneously also dried. The duration of the heat treatment is limited by the risk that the desired profile of properties of the polymer material is destroyed owing to the action of heat.

Before, during or after the postcrosslinking step, the surface of the polymer materials, or of the hydrogel having a microporous structure, is brought into contact with aluminum salts, preferably with aluminum lactate. It is particularly preferable for the treatment with the aluminum salts to be carried out at the same time as the surface postcrosslinking step by bringing a preferably aqueous solution containing the postcrosslinker and also the aluminum salt(s), preferably aluminum lactate, into contact with the particulate absorbent polymer material having a microporous structure, or with the hydrogel having a microporous structure, and then heating.

It is preferable here for the aluminum salts to be brought into contact with the polymer material/hydrogel in an amount ranging from 0.01 to 30% by weight, more preferably in an amount ranging from 0.1 to 20% by weight and even more preferably in an amount ranging from 0.3 to 5% by weight (if present as hydrate, reckoned on an anhydrous basis), all based on the weight of the particulate absorbent polymer material having a microporous structure or, respectively, of the hydrogel having a microporous structure.

Preferred aluminum salts are particularly $AlCl_3 \times 6H_2O$, $NaAl(SO_4)_2 \times 12\ H_2O$, $KAl(SO_4)_2 \times 12\ H_2O$ or $Al_2(SO_4)_3 \times 14\text{-}18\ H_2O$, aluminum lactate or else water-insoluble aluminum compounds, for instance aluminum oxides, for example $Al_2O_3$, or aluminates. Particular preference is given to using aluminum lactate, aluminum sulphate or mixtures of aluminum lactate and aluminumسulphate.

A contribution to solving the problems defined at the beginning is also made by an absorbent core containing an upper substrate layer, a lower substrate layer and an absorption layer arranged between the upper and the lower substrate layers,
wherein the absorption layer includes a particulate absorbent polymer material according to the invention and less than 0.1 g, particularly preferably less than 0.05 g and most preferably less than 0.01 g of cellulose fibers per gram of particulate absorbent polymer material.

"Absorbent core" for the purposes of the present invention is preferably understood as meaning a construction which in the case of an absorbent article, for instance a diaper, can be arranged between the upper ply, impermeable to aqueous fluids and facing away from the body side of the wearer, and the lower ply, permeable to aqueous fluids and facing the body side of the wearer, and the primary function of which is to absorb and store the fluids, for example blood or urine, which have been imbibed by the absorbent article. The absorbent core itself preferably comprises no imbibition system, no upper ply and no lower ply of the absorbent article.

However, what is most preferable according to the present invention is for the absorbent core to be essentially free of cellulose fibers. The formulation "essentially free of cellulose fibers" is used herein to describe an article, such as an absorbent core, which contains less than 10% by weight of cellulose fibers, less than 5% by weight of cellulose fibers, less than 1% by weight of cellulose fibers, no cellulose fibers or not more than an insignificant amount of cellulose fibers. Cores of this type are more particularly described in WO-A-2008/155722, WO-A-2008/155711, WO-A-2008/155710, WO-A-2008/155702, WO-A-2008/155701, WO-A-2008/155699, EP-A-1 225 857, WO-A-01/15647, WO-A-2011/120504, DE-A-10 2009 049 450, WO-A-2008/117109, WO-A-97/11659, EP-A-0 826 349, WO-A-98/37846, WO-A-95/11653, WO-A-95/11651, WO-A-95/11652, WO-A-95/11654, WO-A-2004/071363 or WO-A-01/89439.

In a preferred embodiment of the absorbent core according to the present invention, the absorbent core contains a thermoplastic material and a multiplicity of compartments containing the particulate absorbent polymer material. Absorbent cores particularly preferred in this context according to the present invention are such constructions as are called and described as absorbent core in WO-A-2008/155722, WO-A-2008/155711, WO-A-2008/155710, WO-A-2008/155702, WO-A-2008/155701 or WO-A-2008/155699. Accordingly, in a particularly preferred embodiment of the present invention, the absorbent core contains layers of a thermoplastic material and a multiplicity of compartments containing the particulate absorbent polymer material, wherein the compartments are each bounded by the upper or lower substrate layer and also by a layer of the thermoplastic material. Such a construction can be realized according to the teaching of the above-cited patent applications by the particulate absorbent polymer material being applied to the particular substrates (upper or lower substrate layer) in clusters of particles to form a grid pattern forming land areas and junction areas between the land areas. "Land areas" are areas in which the thermoplastic material is not in direct contact with the upper or lower substrate layer. "Junction areas" are areas in which the thermoplastic material is in direct contact with the upper or lower substrate layer. The junction areas in the grid pattern include little or no particulate absorbent polymer material. The land areas and junction areas can take a multitude of forms/shapes which include but are not limited to circular, oval, square, rectangular, triangular and the like.

One example of an absorbent core according to the present invention is a core containing a first sub-layer and a second sub-layer adjoining the first sub-layer, wherein the first sub-layer contains the upper substrate layer and also compartments containing the particulate absorbent polymer material which are bounded by the upper substrate layer and a first layer of a thermoplastic material, and the second sub-layer contains the lower substrate layer and also compartments containing the particulate absorbent polymer material which are bounded by the lower substrate layer and a second layer of a thermoplastic material, wherein the first layer of thermoplastic material adjoins the second layer of thermoplastic material. This construction corresponds to the construction shown by way of example in FIGS. 7A and 7B of WO-A-2008/155722.

The thermoplastic material in the preferred design of the absorbent core according to the present invention serves primarily to cover and at least partially immobilize the particulate absorbent polymer material on the upper or lower substrate layer. In one embodiment of the present invention, the thermoplastic material can be in an essentially uniform arrangement within the particulate absorbent polymer material between the polymers. However, in one specific embodiment, the thermoplastic material may be a fiber layer which is at least partly in contact with the particulate absorbent polymer material and partly in contact with the upper or lower substrate layer, as shown for instance in FIGS. 3 and 4 of WO-A-2008/155722. In this case, the layer of thermoplastic material may be obtainable by melting a fibrous thermoplastic material for example.

Preferred materials for the upper and lower substrate layers and also for the thermoplastic material are those materials which are described by way of example in WO-A-2008/155722 as materials that are preferred for these components.

The manner of producing absorbent cores of this type is preferably equal to the manner described by way of example in WO-A-2008/155699. Accordingly, the process comprises the steps of depositing the particulate absorbent polymer material on the lower substrate layer in a first pattern to form a first absorbent layer such that the particulate absorbent polymer material is discontinuously distributed on the lower substrate layer;

depositing the particulate absorbent polymer material on the upper substrate layer in a second pattern to form a second absorbent layer such that the particulate absorbent polymer material is discontinuously distributed on the upper substrate layer;

depositing the layer of thermoplastic material on the particulate absorbent polymer material and the lower and upper substrate layer to cover the particulate absorbent polymer material on the lower and upper substrate layers; and combining the first and second absorbent layers together such that at least one portion of the thermoplastic material of the first absorbent layer contacts at least one portion of the thermoplastic material of the second absorbent layer.

A contribution to solving the problems defined at the outset is also made by a hygiene article containing an absorbent core of the present invention, this hygiene article preferably being a diaper. A diaper typically contains a lower ply permeable to fluids (which when the diaper is being worn faces the body side of the diaper wearer), an upper ply essentially impermeable to fluids (which when the diaper is being worn faces away from the body side of the diaper wearer) and also the absorbent core of the present invention, which is arranged between the lower ply and the upper ply. The hygiene article in addition to these three components may also contain further components, for instance a reclosable fastening system as described by way of example in WO-A-2008155699, or a further acquisition layer localized between the lower ply permeable to fluids and the absorbent core of the present invention, as described by way of example in WO-A-2008/155722. A diaper construction preferred according to the present invention is shown by way of example in FIG. 1 of WO-A-2008/155722.

A contribution to solving the problems defined at the outset is also made by a process for producing an absorbent core containing an upper substrate layer, a lower substrate layer and also an absorption layer arranged between the upper and the lower substrate layers, wherein the absorption layer comprises a particulate absorbent polymer material and less than 0.1 g of cellulose fibers per gram of particulate absorbent polymer material, containing the steps of A) providing a particulate absorbent polymer material according to the invention;

B) incorporating the particulate absorbent material in an absorbent core.

Incorporating the particulate material in the absorbent core comprises for example the process steps of B1) depositing the particulate absorbent polymer material on the lower substrate layer in a first pattern to form a first absorbent layer such that the particulate absorbent polymer material is discontinuously distributed on the lower substrate layer;

B2) depositing the particulate absorbent polymer material on the upper substrate layer in a second pattern to form a second absorbent layer such that the particulate absorbent polymer material is discontinuously distributed on the upper substrate layer;

B3) depositing the layer of thermoplastic material on the particulate absorbent polymer material and the lower and upper substrate layer to cover the particulate absorbent polymer material on the lower and upper substrate layers; and B4) combining the first and second absorbent layers together such that at least one portion of the thermoplastic material of the first absorbent layer contacts at least one portion of the thermoplastic material of the second absorbent layer.

A contribution to solving the problems defined at the outset is also made by a process for producing an absorbent core containing an upper substrate layer, a lower substrate layer and also an absorption layer arranged between the upper and the lower substrate layers, wherein the absorption layer comprises a particulate absorbent polymer material and less than 0.1 g of cellulose fibers per gram of particulate absorbent polymer material, containing the steps of a) selecting a suitable particulate absorbent polymer material on the basis of the results of determining the product of (swell index) and permeability index (=APC value) for at least one time t, after adding a fluid to the particulate absorbent polymer structure;

b) incorporating a particulate absorbent material thus selected in the absorbent core, wherein preferred constructions for absorbent cores are the constructions already described as preferred at the beginning in connection with the absorbent core of the present invention.

In one preferred embodiment of the process according to the present invention, step a) comprises determining the product of swell index$^2$ and permeability index (=APC value) for at least 11 different times t, and selecting the particulate absorbent polymer material on the basis of the sum total of all APC values obtained.

A contribution to solving the problems defined at the outset is also made by an absorbent core that is obtainable by the processes described above.

The invention will now be more particularly elucidated by means of figures, test methods and non-limiting examples.

FIGURES

Figure 4:
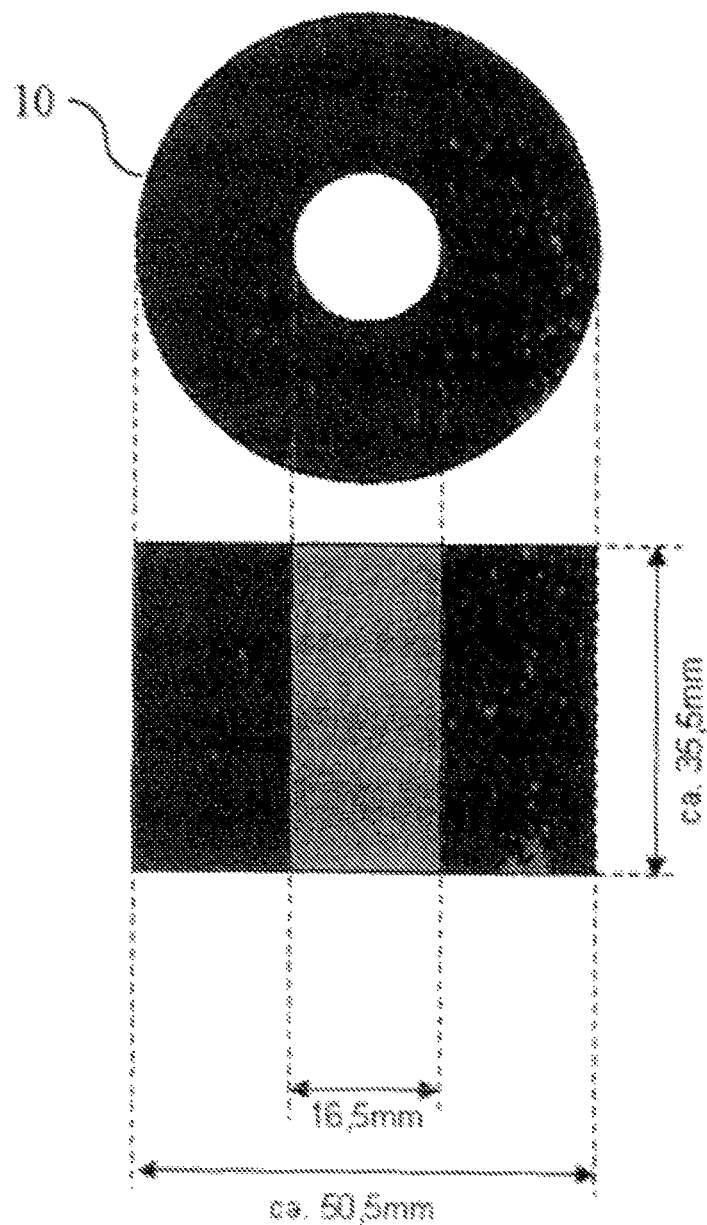

FIG. 4 shows the weight 10 which is placed on the plunger 7. Height and width of the weight 10 depend on the weight of the material used. Total loading due to plunger 7 and weight 10 is 594 g±5 g (corresponds to a loading of 21 g/cm$^2$±0.2 g/cm$^2$). The width of the weight should not exceed 70 mm.

Figure 5:
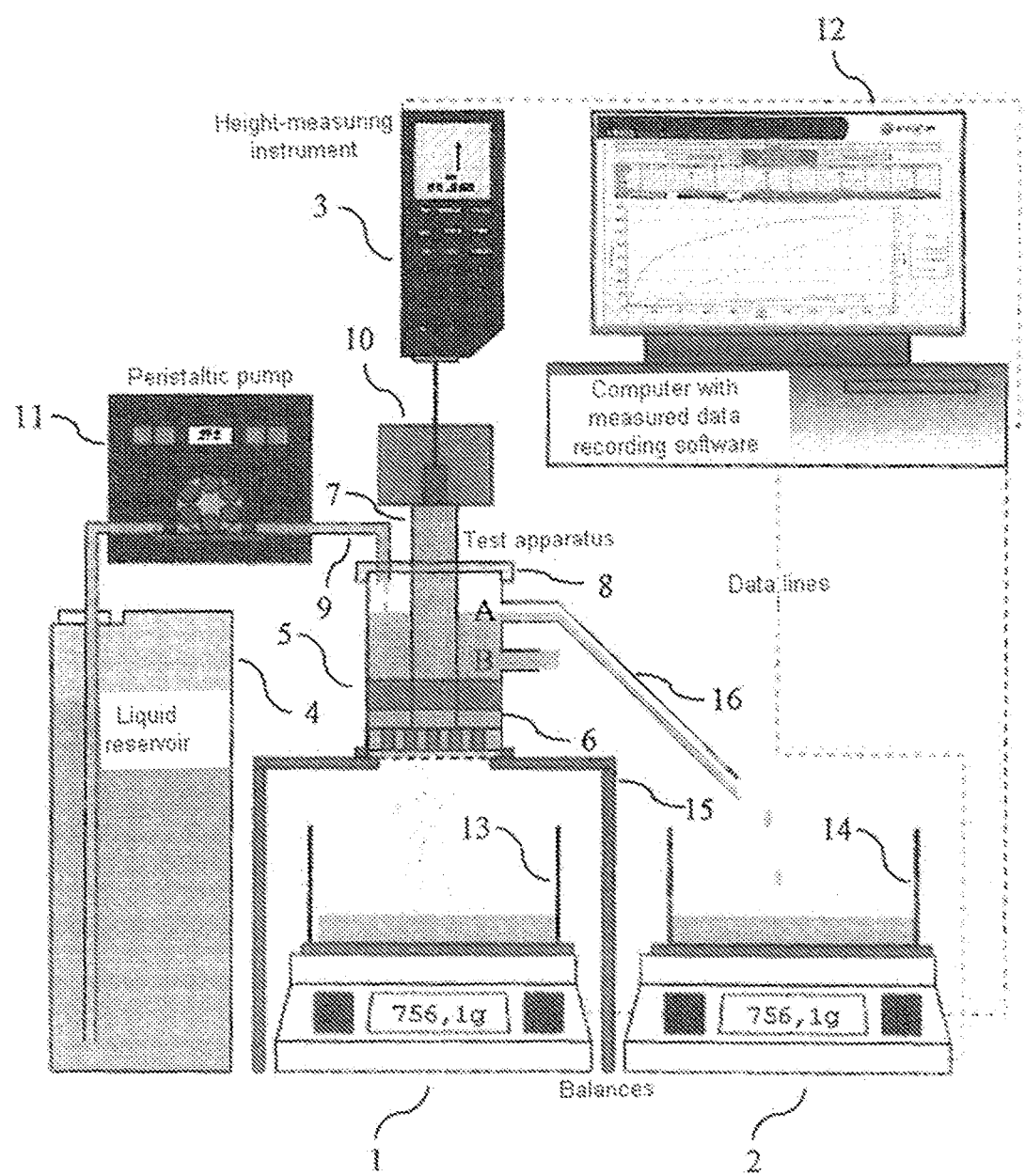

FIG. 5 shows the experimental arrangement involved in determining the APC values.

TEST METHODS

Determining the APC Values
APC values were determined using the measuring arrangement shown in FIG. 5.

1. Principle of Measurement

Figure 1:
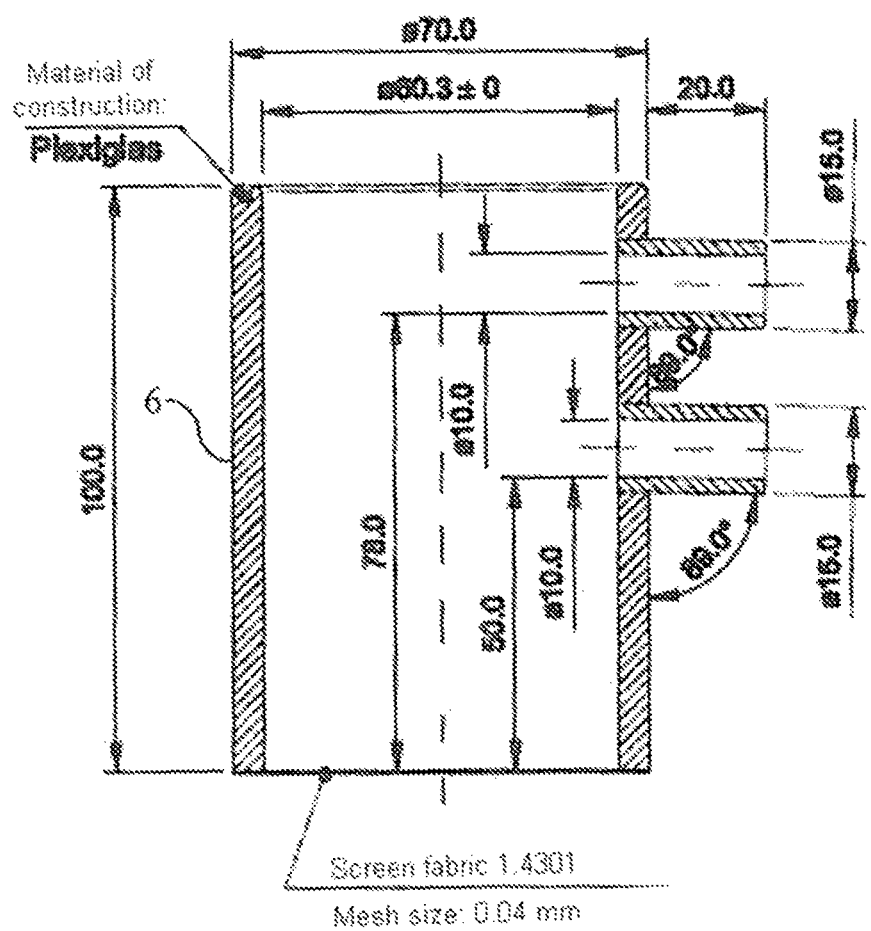
FIG. 1 shows the measuring pot 6 used to determine the APC values with its particular dimensions (in mm)
Figure 2:
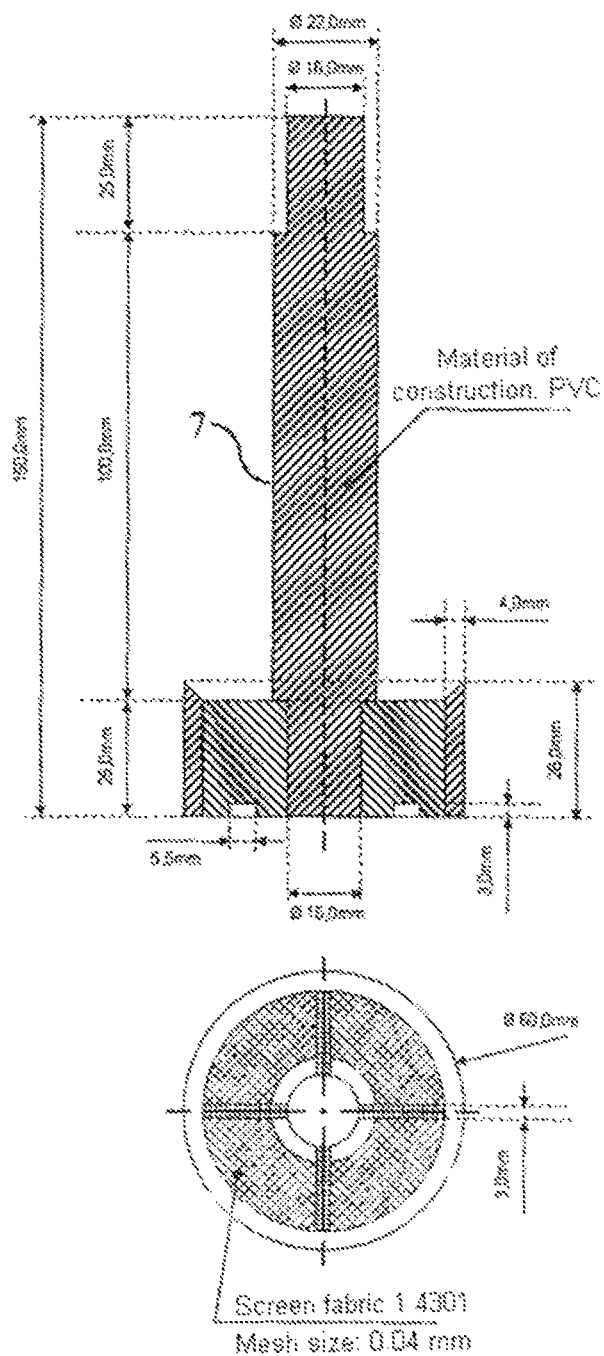
FIG. 2 shows the plunger 7 used for determining the APC values with its particular dimensions (in mm), which is inserted into the measuring pot 6 shown in FIG. 1.

To determine the APC values, 1.800 g (±0.005 g) of the particulate absorbent polymer material to be analyzed (hereinafter referred to as "SAP") are sprinkled into the measuring pot 6 which is shown in FIG. 1 and has a screen fabric as base and uniformly distributed on the screen base. The plunger shown in FIG. 2 is then introduced into the measuring pot and, as shown in FIG. 5, loaded with such a weight 10 (see FIG. 4) that a pressure of 21.0 g/cm$^2$±0.2 g/cm$^2$ (total weight of plunger and weight=594 g±5 g) on the SAP material. The cylinder unit (measuring pot 6, SAP, plunger 7 and weight 10) is placed on a support table 15 having a circularly round cutout, as shown in FIG. 5. The support table 15 stands above a balance 1. A peristaltic pump 11 passes the test solution into the cylinder unit at constant flow rate. Conducted liquid is continually measured in the collecting vessel 13 underneath the support table 15 (on a balance 1). There are outflows A and B in measuring pot 6 at a previously defined height (the lower outflow B in the measuring pot 6 shown in FIG. 1 is closed, as is indicated in FIG. 5). As the gel layer forms, a liquid column can become established up to the height of outflow A. Thereafter, excess liquid exits via the outflow A. This liquid passes through a piece of tube 16, about 10 cm in length, into a collecting vessel 14 and is continually measured on a balance 2. Throughout the entire measurement, the height of the developing gel layer is likewise measured continually. All measurements (balances, height measurement) are automatically captured and stored.

When measurement conditions (amount of weighed-in SAP in g, pressure on SAP in g/cm$^2$, feed stream of test solution to cylinder unit in g/sec) are chosen to be constant, the following measurement data ($\sigma$1) to ($\sigma$3) are accordingly continuously captured:

($\sigma$1) changing height of developing gel layer by height-measuring instrument 3;

($\sigma$2) changing weight on balance 1 at left in FIG. 5 due to the test liquid passing through the gel layer;

($\sigma$3) changing weight on balance 2 at right in FIG. 5 due to the test liquid exiting via outflow A.

2. Measuring Instruments Used 2 balances (1, 2) with an accuracy of min 0.1 g, equipped with a PC interface (e.g. Sartorius CP 8201).

Height-measuring instrument 3 with an accuracy of min 0.1 mm and a measurement length of min. 30 mm, equipped with a PC interface (e.g. Tesa Digico 2).

Liquid reservoir 4 (at least corresponding to the liquid quantity predetermined by the test parameters, for example 30 min at 2 g/s=3600 g).

Test apparatus 5 with loading (see also FIGS. 1 and 2).

Transparent measuring pot 6 of Plexiglas as per FIG. 1, (d1 (Binner)=60.3 mm±0 mm, h=100 mm±0.5 mm) with 2 outflows (of which only the upper one is used and the lower is closed during the measurement) in h1*=55 mm and h2*=83 mm (Binner=10 mm) (*mean height of outflows). The lower side of the measuring pot is equipped with a stainless steel screen fabric (400 mesh=36 μm).

Plastics plunger 7 (d2 (θ outer)=60 mm±0 mm) of PVC as per FIG. 2 (d1−d2=0.3 mm and h=150 mm) The lower side of plastics plunger 7 is equipped with a stainless steel screen fabric (400 mesh=36 μm). The height of the lower part of the plastics plunger 7 is 28 mm. There are 4 struts in this part, which contribute to stabilizing the screen fabric. Each strut is equipped in the lower region (i.e. in the region which is in contact with the steel screen fabric) with an approximately 3×5.5 mm passageway to ensure uniform distribution of the liquid.

Figure 3:
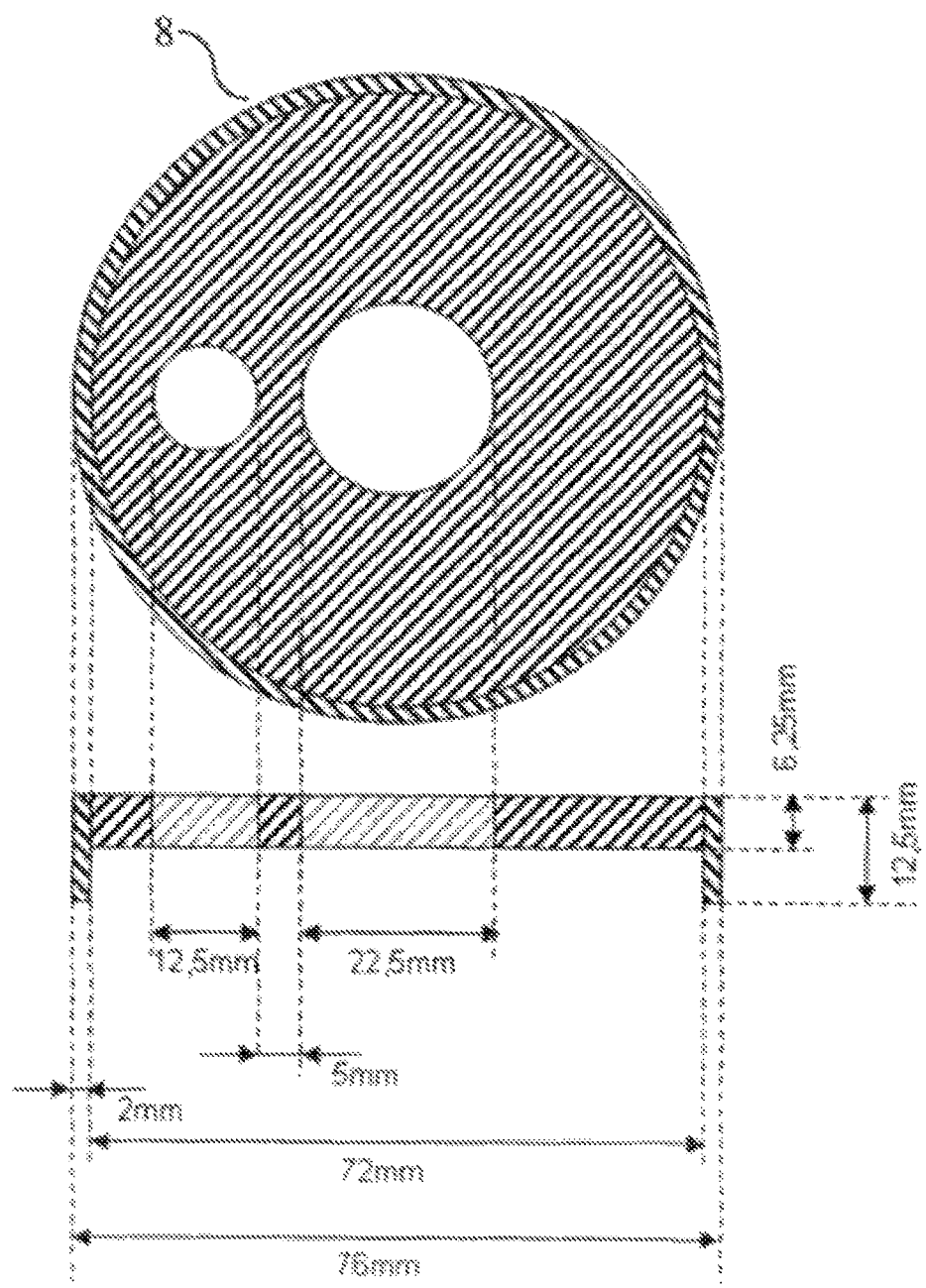
FIG. 3 shows the lid 8, which is made of PVC, for the measuring pot 6.

A close-fitting lid 8 with cutouts for the plastics plunger 7 and the liquid feed 9 (see FIG. 3).

Weight 10, which is placed on the plastics plunger 7 (see FIG. 4). Plastics plunger 7 and weight 10 together have to attain the defined weight. The standard here is a total mass of 594 g±5 g (corresponds to a loading of about 21 g/cm²±0.2 g/cm², which corresponds to a pressure of about 0.3 psi).

Liquid pump 11 (a peristaltic pump for example) having a performance of 30 mL/min to 400 mL/min, e.g. Ismatec MCP standard with Ismatec SB-2V pump head and Tygon Standard tubing (ID 4.8, WT 1.6, OD 8.0).

Computer system 12 with appropriate software for recording the balance display & height measurements.

Collecting vessels 13 and 14 for liquid (min. 3.6 L).

Support table 15 with a circularly round cutout (A 6 cm, corresponds exactly to the width of the screen fabric in the measuring pot). This cutout is surrounded by an approximately 2 cm high plastics ring (θ 7.2 cm, corresponds approximately to the outside diameter of the measuring pot) in a centric arrangement (this fixes the cylinder unit during the measurement in order that the liquid may pass through unhindered and the height measurement is always made in the same place).

3. Performing the Measurement

At least one 2-fold determination shall be performed.

Preliminary work:

The liquid reservoir 4 is filled to provide sufficient test liquid (0.9% NaCl solution). The temperature of the test liquid is 23° C.±2.0° C. (room temperature=23° C.±2.0° C., relative humidity 55%±15%).

The peristaltic pump 11 is adjusted in accordance with the intended flow rate. For this it is possible to use either, as far as suitable, the system for measured value recording, or alternatively the requisite amount can also be determined using a stopwatch and a glass beaker or similar. Standard flow rates are 1 and 2 g/s.

The system for measured value recording is assembled. Any system can be used whereby measurement data from balances and height-measuring instruments can be recorded under time control. Such a system can consist for example of a computer with Windows operating system (XP or later), Microsoft Excel (version 6 or later) an RS232 4-fold interface card and programmed Visual Basic for Application module. The system has to be capable of performing all 3 measured value retrievals (σ1) to (σ3) in a time window of not more than 0.5 seconds. Balances 1 and 2 and the height-measuring instrument 3 are connected to the computer 12 (the program for measured value recording has to be adjusted to the appropriate settings (baud rate, parity, etc.) in respect of the balances 1 and 2 and the height-measuring instrument 3.

Measurement:

The SAP sample to be analyzed must be thoroughly commixed. The test material to be removed should be free of clumps and impurities. 1.800 g±0.005 g of SAP are weighed into the test apparatus. The SAP is uniformly distributed on the screen base.

The SAP sample is loaded at 21.0 g/cm²±0.2 g/cm² using the plunger 7 and the weight 10 and placed in the cutout of support table 15. The outflow-equipped tube end from the peristaltic pump (liquid feed 9) is placed over a length of 2-3 cm through the addition aperture in the covering plate 8 of the test apparatus.

The height-measuring instrument 3 is installed with the measuring rod centered on plunger 7 of the test apparatus. During the test period of 30 minutes, the measured values are retrieved every 10 seconds and recorded against the particular time.

Balances 1 and 2 are tared and the height-measuring instrument 3 is zeroed.

The system for measured value recording is initialized.

Directly but in any case not later than 0.5 seconds after initializing the system for measured value recording the addition via the peristaltic pump 11 is started.

On conclusion of the test period, the peristaltic pump 11 is switched off.

4. Evaluation

The data series of height ($h_t$) in mm at time (t) in s (σ1), flow rate (Fl.th.$_t$) in g at time (t) in s (σ2) and overflow (Fl.ov.$_t$) in g at time (t) in s (σ3) can be used to calculate the following further values (each at time t):

$Vzu_t$ in g: liquid volume addition at time t;

$V_t$ in cm³: the gel volume at time t (base area of measuring pot 6=28.27 cm²):

$$V_t[\text{cm}^3]=h_t \text{ [mm]}/10*28.27 \text{ cm}^2 \quad \text{formula:}$$

$\Delta V_t$ in cm³: the gel volume increase within 10 s at time t (base area of measuring pot 6=28.27 cm²:

$$\Delta V_t[\text{cm}^3]=(h_t \text{ [mm]}-h_{t-10} \text{ [mm]})/10*28.27 \text{ cm}^2 \quad \text{formula:}$$

$QI_t$: swell index (dimensionless) at time t (E=starting weight of SAP in g; 1 cm³=1 g is assumed for a 0.9% NaCl solution):

$$QI_t=\Delta V_t[\text{cm}^3]/(E[\text{g}]*10) \quad \text{formula:}$$

$\Delta Fl.th._t$ in g/s: flow rate averaged over 10 s at time t:

$$\Delta Fl.th._t[\text{g/s}]=(Fl.th._t \text{ [g]}-Fl.th._{t-10} \text{ [g]})/10 \text{ s} \quad \text{formula:}$$

$Vü_t$ in g: volume supernatant in APC measuring pot:

$$Vü_t[\text{cm}^3=\text{g}]=Vzu_t \text{ [g]}-V_t \text{ [cm}^3\text{]}-Fl.ov._t \text{ [g]}-Fl.th._t \text{ [g]} \quad \text{formula:}$$

$h(Vü)_t$ in mm: theoretical (calculated) height of liquid in APC pot (taking into account the area of plunger=5 cm²; effective area=28.27 cm²−5 cm²=23.27 cm²):

$$h(Vü)_t[\text{mm}]=(h_t \text{ [mm]}/10+(Vü_t \text{ [g]}/23.27 \text{ cm}^2))*10 \quad \text{formula:}$$

$PI_t$: permeability index (dimensionless) at time t=20 s . . . 120 s:

$$PI_t = \frac{\Delta Flth_i[\text{cm}^3/sec] \times h_i[\text{cm}]}{981 \text{ (cm/sec}^2) \times h(Vü)_i[\text{cm}] \times 28.27 \text{ cm}^2 * 10^{-7} sec} \quad \text{formula}$$

$APC_{i\times 10 \; sec}$; $APC_{i\times 10 \; sec}$ value at time T=20 s . . . 120 s (i=2 to 12), The values described above are further used to determine the $APC_{max}$ value (i.e., highest of the 11 APC values determined), the APC average value $APC_{mean}$ and the sum total of all APC values ($APC_{sum}$).

$$APC_{i \times 10\ sec} = QI_{i \times 10\ sec}^2 * PI_{i \times 10\ sec}$$

$$APC_{mean} = \frac{1}{11}\sum_{i=2}^{12} APC_{i \times 10\ sec}$$

$$APC_{sum} = \sum_{i=2}^{12} APC_{i \times 10\ sec}$$

formulae

EXAMPLES

Comparative Example (Not in Accordance with the Present Invention)

In 1972.90 g of an aqueous solution of sodium acrylate having a degree of neutralization of 70 mol % (based on acrylic acid) and a total monomer concentration of 39.37% are dissolved 1.770 g of polyethylene glycol 300 diacrylate (0.2% based on acrylic acid/ester content=72%) and 2.560 g of polyethylene glycol 440 monoallyl ether acrylate (0.4% based on acrylic acid/ester content=100%) as crosslinker. The monomer solution is purged with nitrogen for 30 minutes in a plastics polymerization vessel to remove the dissolved oxygen. At a temperature of 4° C., the polymerization is started by the successive addition of 0.6 g of sodium peroxodisulphate in 10 g of distilled water, 0.14 g of 35% hydrogen peroxide solution in 10 g of distilled water and 0.03 g of ascorbic acid in 2 g of distilled water. On attainment of the final temperature (about 100° C.) the gel is comminuted with a mincer and dried at 150° C. in a circulating air drying cabinet for 2 h. The dried product is coarsely crushed, ground and screened off to a particle size fraction of 150-710 µm. The bulk obtained is screened into individual particle size fractions and mixed together to form a synthetically produced PSD as follows:

>150 µm=15%/>300 µm=48%/>500 µm=32%/>600 µm=5%.

The intermediates thus obtained are postcrosslinked by coating with a solution consisting of ethylene carbonate/water/aluminum lactate/aluminum sulphate in a ratio of 1/3/0.4/0.3% based on 100 g of intermediate and subsequent postheating in a drying cabinet at 170° C., 90 minutes.

Example 1 (In Accordance with the Present Invention)

In 963.60 g of an aqueous solution of sodium acrylate having a degree of neutralization of 70 mol % (based on acrylic acid) and also a total monomer concentration of 40.30% are dissolved 0.775 g of polyethylene glycol 300 diacrylate (0.20% based on acrylic acid/ester content=83%) and 1.639 g of polyethylene glycol 440 monoallyl ether acrylate (0.40% based on acrylic acid/ester content=78%) as crosslinker. This solution is subsequently admixed with 9.6 g of a 10% aqueous solution of the comonomer Pluriol A 23 R (from BASF) and the monomer solution is purged with nitrogen for 30 minutes in a plastics polymerization vessel to remove the dissolved oxygen. At a temperature of 4° C., 2 g of slightly calcined sodium carbonate (from Solvay) are added as blowing agent and the polymerization is started by the successive addition of 0.3 g of sodium peroxodisulphate in 10 g of distilled water, 0.07 g of 35% hydrogen peroxide solution in 10 g of distilled water and 0.015 g of ascorbic acid in 2 g of distilled water. On attainment of the final temperature (about 100° C.) the gel is comminuted with a mincer and dried at 150° C. in a circulating air drying cabinet for 2 h. The dried product is coarsely crushed, ground and screened off to a particle size fraction of 150-710 µm. The bulk obtained is screened into individual particle size fractions and mixed together to form a synthetically produced PSD as follows:

>150 µm=15%/>300 µm=48%/>500 µm=32%/>600 µm=5%.

The intermediates thus obtained are postcrosslinked by coating with a solution consisting of ethylene carbonate/water/aluminum lactate/aluminum sulphate in a ratio of 1/3/0.4/0.3% based on 100 g of intermediate and subsequent postheating in a drying cabinet at 170° C., 90 minutes.

Example 2 (In Accordance with the Present Invention)

In 1962.4 g of an aqueous solution of sodium acrylate having a degree of neutralization of 70 mol % (based on acrylic acid) and also a total monomer concentration of 39.6% by weight are dissolved 1.529 g of polyethylene glycol 300 diacrylate (ester content=83.7%; 0.2% by weight based on acrylic acid) and 3.303 g of polyethylene glycol 440 monoallyl ether acrylate (0.40% by weight based on acrylic acid/ester content=77.5%). Thereafter 10.0 g of sodium carbonate produced in the moving bed spray granulation process and having a particle size of 400-600 µm are added as blowing agent (0.5% by weight based on batch size). The monomer solution is purged with nitrogen for 15-30 minutes to remove the dissolved oxygen. At a temperature of 20° C., the monomer solution, which is admixed with 0.6 g of sodium peroxodisulphate in 10 g of distilled water and 0.14 g of 35% hydrogen peroxide solution in 10 g of distilled water, is transferred into the List Batch CRP 2.5 kneader under inert gas countercurrent and shaft agitation. The target settings and hence the desired parameters during the reaction in the twin-shaft, corotating batch-operated kneading reactor and/or the peripherals are: temperature of oil in heating circuit of reactor shell: 75° C.; shaft speed: 60 revolutions per minute. After the monomer solution has been transferred into the reactor interior, the sodium carbonate is added. After it has been stirred in for 30 seconds, 0.030 g of ascorbic acid in 2 g of distilled water is introduced into the reaction interior, and the exothermic reaction is started. The target value for the oil in the heating circuit of the reactor shell is set to 100° C. After 5 minutes have elapsed, the heating circuit is switched off After altogether 10 minutes the cororating shafts are stopped, the reactor is opened, the hydrogel formed is removed and dried in a circulating air drying cabinet at 150° C. for 2 hours. The dried product is crushed, ground with a cutting mill from Retsch and a cutting sprocket of 2 mm hole size, screened into individual particle size fractions and mixed together to form a synthetic particle size distribution as follows:

>150 µm=15%/>300 µm=48%/>500 µm=32%/>600 µm=5%.

Postcrosslinking is affected by coating with a solution consisting of ethylene carbonate/water/aluminum lactate/aluminum sulphate in a ratio of 1/4/0.4/0.3% based on 100 g of intermediate and also subsequent postheating in a drying cabinet at 175° C., 90 minutes.

Example 4

The polymers obtained in the comparative example and in Examples 1 and 2 are measured for the $APC_{max}$ value and the $APC_{sum}$ value using the test method described herein. The results are shown in Table 3. The measurements obtained continuously for a period of 120 seconds in the determination of the APC parameters and the measurement data derived therefrom purely arithmetically in respect of the APC analysis of the polymer from the comparative example are illustratively compiled in Tables 1 and 2.

TABLE 1 the directly obtained measurements (o1), (o2) and (o3)

| Time t [s] | ht [mm] | Time t [s] | Fl.th.t [g] | Time t [s] | Fl.ov.t [g] |
|---|---|---|---|---|---|
| 0 | 0.00 | 0 | 0.50 | 0 | 0.01 |
| 10 | 0.28 | 10 | 4.65 | 10 | 0.01 |
| 20 | 1.22 | 20 | 15.35 | 20 | 0.00 |
| 30 | 2.15 | 30 | 27.77 | 30 | 0.00 |
| 40 | 2.96 | 40 | 41.20 | 40 | 0.00 |
| 50 | 3.65 | 50 | 55.07 | 50 | 0.00 |
| 60 | 4.27 | 60 | 69.80 | 60 | 0.00 |
| 70 | 4.87 | 70 | 85.12 | 70 | 0.00 |
| 80 | 5.41 | 80 | 100.63 | 80 | 0.00 |
| 90 | 5.92 | 90 | 116.13 | 90 | 0.01 |
| 100 | 6.42 | 100 | 131.55 | 100 | 0.01 |
| 110 | 6.88 | 110 | 147.15 | 110 | 0.02 |
| 120 | 7.31 | 120 | 162.88 | 120 | 0.01 |

TABLE 2 measured quantities obtained arithmetically from the measurements of Table 1

| Time (sec) | $DV_t$ [cm³] | $QI_t$ | $DFl.th._t$ [g/s] | $Vzu_t$ [g] | $V_t$ [cm³] | $Vü_t$ [cm³] | $h(Vü)_t$ [mm] | $PI_t$ | APC value[1] |
|---|---|---|---|---|---|---|---|---|---|
| 0 | 0.00 | 0.00 | 0.50 | 0 | 0.01 | 0.00 | 0.00 | | |
| 10 | 0.78 | 0.04 | 0.42 | 20 | 0.79 | 14.55 | 6.53 | 6.42 | |
| 20 | 2.67 | 0.15 | 1.07 | 40 | 3.46 | 21.19 | 10.33 | 45.72 | 1.01 |
| 30 | 2.62 | 0.15 | 1.24 | 60 | 6.08 | 26.14 | 13.39 | 72.03 | 1.53 |
| 40 | 2.28 | 0.13 | 1.34 | 80 | 8.36 | 30.44 | 16.04 | 89.31 | 1.43 |
| 50 | 1.97 | 0.11 | 1.39 | 100 | 10.33 | 34.59 | 18.52 | 98.69 | 1.19 |
| 60 | 1.75 | 0.10 | 1.47 | 120 | 12.08 | 38.11 | 20.65 | 109.86 | 1.04 |
| 70 | 1.67 | 0.09 | 1.53 | 140 | 13.75 | 41.12 | 22.54 | 119.25 | 1.03 |
| 80 | 1.53 | 0.08 | 1.55 | 160 | 15.28 | 44.09 | 24.35 | 124.10 | 0.90 |
| 90 | 1.46 | 0.08 | 1.55 | 180 | 16.75 | 47.12 | 26.17 | 126.36 | 0.84 |
| 100 | 1.39 | 0.08 | 1.55 | 200 | 18.14 | 50.30 | 28.03 | 127.54 | 0.76 |
| 110 | 1.30 | 0.07 | 1.56 | 220 | 19.44 | 53.39 | 29.82 | 129.55 | 0.68 |
| 120 | 1.23 | 0.07 | 1.57 | 240 | 20.67 | 56.45 | 31.57 | 131.22 | 0.61 |

[1] as mean value of a fourfold determination

TABLE 3

APC parameters of polymers from the comparative example and Examples 1 and 2

| Polymer | $APC_{max}$ | $APC_{sum}$ | CRC [g/g] | AAP [b/b] |
|---|---|---|---|---|
| Comparative example | 1.53 | 11.0 | | |
| Example 1 | 7.01 | 37.3 | 26.1 | 25.3 |
| Example 2 | 3.47 | 18.9 | 25.9 | 25.2 |

Example 5

The polymers obtained in the comparative example and Examples 1 and 2 are used to produce an absorbent core which is in accordance with the present invention.

A cut-to-size nonwoven (article No. 00028710 from Freudenberg) having the dimensions of 12×12 cm is uniformly sprayed with adhesive (Dispomelt CS 22 from Henkel) using a pneumatic hot-melt adhesive gun from Bühnen, type HB 710 spray inc. twist nozzle set standard θ 1.5 mm, operated at 4 bar compressed air, for 30 seconds. The spray gun is adjusted beforehand to a melting temperature of 160° C. Exactly 5 g of SAP are uniformly sprinkled onto a previously marked/centered area of 10×10 cm. A further nonwoven having the same dimensions is sprayed with the adhesive in the same way and then placed with the adhesive side down onto the SAP ply to obtain an absorbent core having the following layer sequence:

nonwoven
adhesive
SAP
adhesive
nonwoven.

This was followed by pressing the layers together using a hand roller. The absorbent core was subsequently stored for one hour to dry the adhesive before the core was measured.

To determine the absorption properties of the absorbent core, the core to be tested was weighed and placed on a wire mesh having a mesh size of 9×9 mm (wire thickness 1 5 mm) and an external size of 12×12 cm, which was placed in a Petri dish using four approximately 1.2 cm high metal feet positioned at the corners of the wire mesh. The absorbent core is loaded with a weight of 200 g using a test plate (10×10 cm). This test plate is equipped in the middle with an addition tube 20 cm in height and 20 mm in inside diameter. This addition tube can be used to pass test fluid through the test plate onto the absorbent core while the absorbent core is under the pressure of the test plate.

Four times in succession 25 g at a time of a 0.9% NaCl solution slightly colored with acid fuchsine are introduced into the addition tube (delay time between the individual additions: 15 minutes). The absorbent core is weighed before the first addition (w1). The test solution is in each case added via the addition tube. On complete imbibition of liquid (4×25 g=100 g) the absorbent core is reweighed (w2). The leakage amount (1) can be determined arithmetically from the difference between the added liquid quantity w0 and the difference in the weight of the absorbent core before and after absorption ($l = w_0 - (w2 - w1)$).

The following measurements were obtained:

TABLE 4

Leakage values of polymers from the comparative example and Examples 1 and 2 in an absorbent core of the present invention

| Polymer | Leakage [g] after fourfold addition |
|---|---|
| Comparative example | 18.7 |
| Example 1 | 8.4 |
| Example 2 | 12.9 |

What is claimed is:

1. A method for preparing a low cellulose content absorbent core by selecting a particulate superabsorbent polymer material for incorporating the particulate absorbent polymer material in an absorbent core containing an upper substrate layer, a lower substrate layer and also an absorption layer arranged between the upper and the lower substrate layers, wherein the absorption layer comprises the particulate absorbent polymer material and less than 0.1 g of cellulose fibres per gram of particulate absorbent polymer material, containing the steps of
A) identifying a particulate absorbent polymer material having at least one of the following properties:
 i) a maximum $APC_{i \times 10\ sec}$ value $\geq 1.6$ for at least one number i selected from the group of integers from 2 to 12; and/or
 ii) a value $\geq 12$ for the sum total of all $APC_{i \times 10\ sec}$ sec values for all numbers i from the group of integers from 2 to 12;
wherein $APC_{i \times 10\ sec}$ value is defined as follows:
$APC_{i \times 10\ sec}$ value=$(QI_{i \times 10\ sec}$ value$)^2 \times PI_{i \times 10\ sec}$ value, where
 the $QI_{i \times 10\ sec}$ sec value is the value of the swell index determined i×10 seconds after adding a 0.9% by weight NaCl solution, and
 the $PI_{i \times 10\ sec}$ value is the value of the permeability index determined i×10 seconds after adding the 0.9% by weight NaCl solution; and
B) incorporating the particulate absorbent material in an absorbent core.

2. The method according to claim 1, wherein the particulate absorbent polymer material has the following property:
i) a maximum $APC_{i \times 10\ sec}$ value $\geq 1.6$ for at least one number i from the group of integers from 2 to 12.

3. The method according to claim 2, wherein the particulate absorbent polymer material has the following property:

i) a maximum $APC_{i \times 10\ sec}$ value $\geq 2.0$ for at least one number i from the group of integers from 2 to 12.

4. The method according to claim 3, wherein the particulate absorbent polymer material has the following property:
i) a maximum $APC_{i \times 10\ sec}$ value $\geq 2.4$ for at least one number i from the group of integers from 2 to 12.

5. The method according to claim 1, wherein the particulate absorbent polymer material has the following property:
ii) a value $\geq 12$ for the sum total of all $APC_{i \times 10\ sec}$ values for all numbers i from the group of integers from 2 to 12.

6. The method according to claim 5, wherein the particulate absorbent polymer material has the following property:
ii) a value $\geq 18$ for the sum total of all $APC_{i \times 10\ sec}$ values for all numbers i from the group of integers from 2 to 12.

7. The method according to claim 6, wherein the particulate absorbent polymer material has the following property:
ii) a value $\geq 24$ for the sum total of all $APC_{i \times 10\ sec}$ values for all numbers i from the group of integers from 2 to 12.

8. The method according to claim 1, wherein the absorbent core is essentially free of cellulose fibers.

9. The method according to claim 1, wherein the absorbent core contains a thermoplastic material and a multiplicity of compartments containing the particulate absorbent polymer material.

10. The method according to claim 9, wherein the absorbent core contains layers of a thermoplastic material and a multiplicity of compartments containing the particulate absorbent polymer material, wherein the compartments are each bounded by the upper or lower substrate layer and also by a layer of the thermoplastic material.

11. The method according to claim 10, wherein the absorbent core contains a first sub-layer and a second sub-layer adjoining the first sub-layer, wherein the first sub-layer contains the upper substrate layer and also compartments containing the particulate absorbent polymer material which are bounded by the upper substrate layer and a first layer of a thermoplastic material, and the second sub-layer contains the lower substrate layer and also compartments containing the particulate absorbent polymer material which are bounded by the lower substrate layer and a second layer of a thermoplastic material, wherein the first layer of thermoplastic material adjoins the second layer of thermoplastic material.

12. The method according to claim 10, wherein at least one layer of a thermoplastic material is obtainable by melting a fibrous thermoplastic material.

* * * * *